United States Patent
Hieronimi et al.

(10) Patent No.: US 8,387,187 B2
(45) Date of Patent: Mar. 5, 2013

(54) POSITIONING SYSTEM

(75) Inventors: Christian Hieronimi, Schwabmunchen (DE); Robert Mitterhauser, Schwabmunchen (DE)

(73) Assignee: Elekta AB (Publ) (SE)

( * ) Notice: Subject to any disclaimer, the term of this patent is extended or adjusted under 35 U.S.C. 154(b) by 246 days.

(21) Appl. No.: 12/668,502

(22) PCT Filed: Jul. 11, 2007

(86) PCT No.: PCT/EP2007/006169
§ 371 (c)(1),
(2), (4) Date: Jan. 11, 2010

(87) PCT Pub. No.: WO2009/006925
PCT Pub. Date: Jan. 15, 2009

(65) Prior Publication Data
US 2010/0186170 A1   Jul. 29, 2010

(51) Int. Cl.
*A47C 27/08* (2006.01)
*A47C 27/00* (2006.01)

(52) U.S. Cl. .......... 5/731; 5/733; 5/734; 5/657

(58) Field of Classification Search .......... 5/689, 640, 5/644, 657, 694, 697, 702, 709, 731–734, 5/655.4, 911, 913
See application file for complete search history.

(56) References Cited

U.S. PATENT DOCUMENTS

| | | |
|---|---|---|
| 3,762,404 A | 10/1973 | Sakita |
| 4,254,518 A | 3/1981 | Buhren et al. |
| 4,768,248 A * | 9/1988 | O'Sullivan ............ 5/640 |
| 5,154,185 A | 10/1992 | Latimer |
| 5,797,153 A * | 8/1998 | Amioka ............ 5/632 |

(Continued)

FOREIGN PATENT DOCUMENTS

| | | |
|---|---|---|
| DE | 4324508 A1 | 1/1995 |
| DE | 4447431 A1 | 6/1996 |

(Continued)

OTHER PUBLICATIONS

International Search Report, Mar. 19, 2008.

*Primary Examiner* — Michael Trettel
(74) *Attorney, Agent, or Firm* — Westman, Champlin & Kelly, P.A.; Z. Peter Sawicki

(57) ABSTRACT

A positioning system for a body comprises a flexible bag of a gas-impermeable material/including a valve to permit evacuation of the interior thereof, the bag containing a flowable granular material and at least one bolster. The body can be at least part of a human form, such as a patient. Systems are generally provided for specific body regions such as the hip or thorax, and for the whole body. The bolster is larger than the grains of the granular material. A size dimension of the bolster is therefore preferably at least 5 times the- size dimension of the granular material, although it sill usually be one or more orders of magnitude larger. Various forms of bolster are possible. A bolster that includes a generally flat section and an upstanding section extending therefrom can be used to locate a shoulder region of the patient in a reproducible yet comfortable form. A bolster that is generally cylindrical in shape can be used to support various areas of a patient such as the neck or knee. The granular material can consist of polystyrene spheres. The bag is preferably of a nylon material; such as a nylon material coated with a polyurethane-based coating.

18 Claims, 2 Drawing Sheets

U.S. PATENT DOCUMENTS

| | | | | |
|---|---|---|---|---|
| 5,832,550 A | * | 11/1998 | Hauger et al. | 5/621 |
| 5,906,205 A | * | 5/1999 | Hiebert | 128/845 |
| 6,226,820 B1 | * | 5/2001 | Navarro | 5/655.5 |
| 6,952,848 B1 | * | 10/2005 | Strunk-Fellows | 5/636 |

FOREIGN PATENT DOCUMENTS

| | | |
|---|---|---|
| DE | 19506270 A1 | 8/1996 |
| EP | 1166740 A | 1/2002 |

\* cited by examiner

POSITIONING SYSTEM

This Application is a Section 371 National Stage Application of International Application No. PCT/EP2007/006169, filed Jul. 11, 2007 and published as WO 2009/006925 A1 on Jan. 15, 2009, the content of which is hereby incorporated by reference in its entirety.

FIELD OF THE INVENTION

The present invention relates to a positioning system.

BACKGROUND ART

Patient positioning systems are used for the accurate and reproducible positioning of patients for radiation therapy, diagnostic imaging, surgery and other medical procedures. For modern radiotherapy treatments, precise positioning of the patient is an indispensable prerequisite.

Typically, such positioning systems use a mouldable vacuum cushion in order to combine patient comfort with reproducible accuracy of the patient's position. The vacuum cushion consists of a hull material, typically a nylon cloth laminated with a polyurethane coating, a filling material such as polystyrene grains, and a valve.

In order to form the cushion into a mould, the patient is placed on the vacuum cushion which then deforms to a shape that accommodates the patient. The tube is that connected to a vacuum supply such as one from a vacuum pump. This generates a vacuum in the cushion, and the vacuum cushion is moulded to the patient's contours. The grains that were previously free-flowing are constrained by compression resulting from the atmospheric pressure on the outside of the cushion.

Typical characteristics of such cushions include
  reproducible positioning of the patient from imaging to treatment and subsequent treatment fractions, while preserving patient comfort and improving the clinical workflow
  optimisation of clinical workflow for a range of clinical setups and indications such as thorax, hip, full body and head and neck
  a comfortable, stable and precise mould of the patient's position Such vacuum cushions are typically constructed entirely of radio translucent materials to provide consistent artefact-free image clarity with minimal dose attenuation.

A coated nylon material for the exterior of the cushion enables smooth mould definition, comfortable patient positioning and ease of cleaning.

SUMMARY OF THE INVENTION

The present invention therefore provides a positioning system for a body, comprising a flexible bag of a gas-impermeable material, including a valve to permit evacuation of the interior thereof, the bag containing a flowable granular material and at least one bolster, which will generally be of a non- or semi-flowable material.

The body can be at least part of a human form, such as a patient. Systems are generally provided for specific body regions such as the hip or thorax, and for the whole body. The bolster is larger than the grains of the granular material. A size dimension of the bolster is therefore preferably at least 5 times the size dimension of the granular material, although it will usually be one or more orders of magnitude larger.

Various forms of bolster are possible. A bolster that includes a generally flat section and an upstanding section extending there from can be used to locate a shoulder region of the patient in a reproducible yet comfortable form. A bolster that is generally cylindrical in shape can be used to support various areas of a patient such as the neck or knee.

The granular material can consist of polystyrene spheres with a general particle size of 0.5 to 3 mm.

The bag is preferably of a nylon material, such as a nylon material coated with a polyurethane-based coating.

BRIEF DESCRIPTION OF THE DRAWINGS

An embodiment of the present invention will now be described by way of example, with reference to the accompanying figures in which.

DETAILED DESCRIPTION OF THE EMBODIMENTS

Embodiments of the present invention generally adopt the structure of a patient positioning system as described above in relation to the background art, thus using mouldable vacuum cushion in order to position the patient comfortably in a reproducible manner. The vacuum cushion consists of a hull material, typically a nylon cloth laminated with a polyurethane-based coating, together with a filling material such as polystyrene grains. A valve is provided on the hull material in order to allow it to be evacuated through connection to a vacuum source or a vacuum pump, or the like. Once evacuated, the atmospheric pressure acting on the hull material compresses the filling material thereby preventing further flow, and the positioning system adopts a rigid or a substantially rigid state for so long as the vacuum is maintained. When the vacuum is broken, the filling material once again becomes flowable and the vacuum cushion can be adapted to a different shape to conform to a new patient, for example. Once formed into the new appropriate shape, the whole material is again evacuated via the valve and the cushion becomes rigid once again.

Embodiments of the present invention further include some form of structural component within the cushion, such as a knee cushion, a neck cushion or a shoulder retractor. As a result, moulding of the vacuum cushion to the patient's contour can be improved in respect of mould definition and shape rigidity through these predefined and integrated structures. These also simplify the handling and moulding to the patient's contour of the cushion as a result in a higher overall quality of the moulding.

Generally, the structural components can be moved relatively freely in the non-evacuated cushion. By evacuating the cushion, the structural components become a single unit together with the remainder of the cushion, due to the pressure of the filling material.

Figure 1:
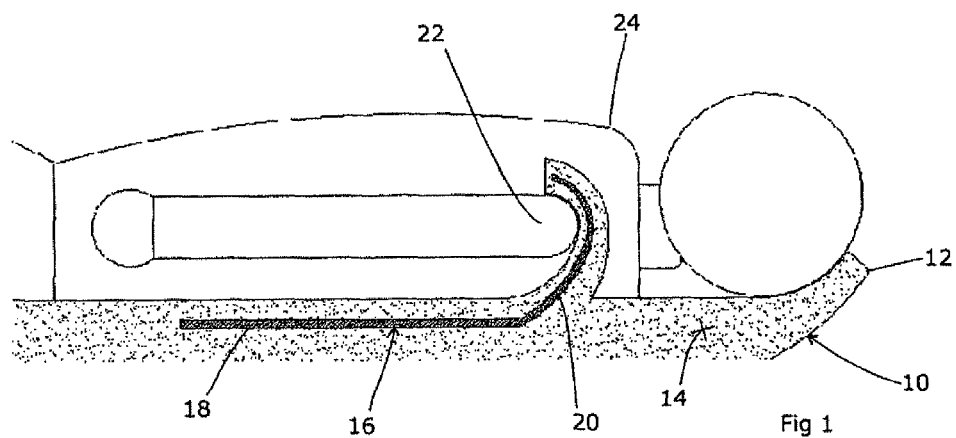
FIG. 1 shows a vertical section through a first embodiment of the invention.

FIG. 1 shows one such example. The cushion 10 consists of a hull material 12 and a filler 14, and also includes a plastics (and/ or fiber reinforced) shoulder retractor 16 generally shaped so as to include a generally flat section 18 that extends underneath a patient's back, from one end of which extends an upstanding part 20 that reaches up and over the shoulder 22 of a patient 24.

With the cushion 10 in the non-evacuated state, the shoulder retractor and the patient can be positioned as required and the patient made comfortable in the cushion. The cushion 10 can then be evacuated to "freeze" the shoulder retractor 16 in the required position. This will mean that, during treatment, the shoulders are held out of the beam and the neck region can be stretched so as to result in improved repositioning of the tumour.

Figure 2:
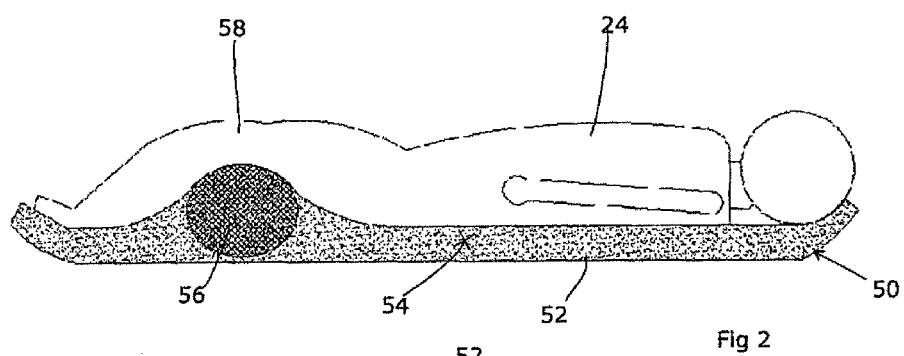
FIG. 2 shows a vertical section through a second embodiment of the invention.
Figure 3:
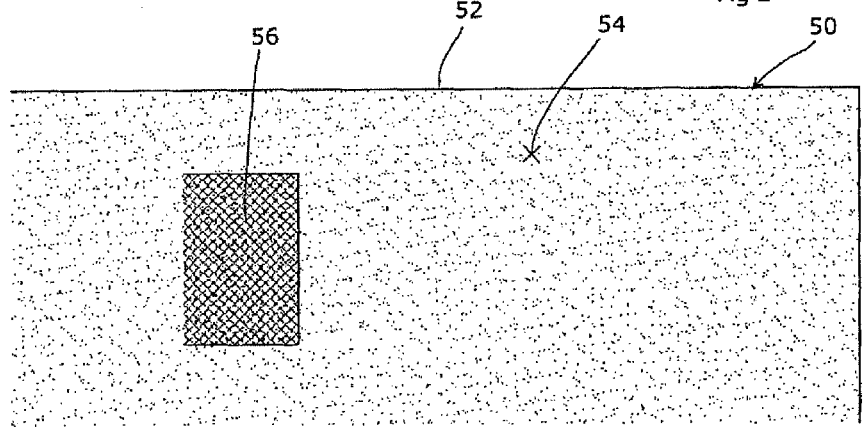
FIG. 3 shows a horizontal section through a second embodiment of the invention.

FIG. 2 shows an alternative arrangement. A cushion 50 includes a hull material 52 and a filling 54, together with an integrated knee cushion 56 of textile filled with polystyrene. This means that the knee or knees 58 of the patient 24 are elevated during treatment, which is known to move the rectum out of the beam in applications involving delivery of radiotherapy to the pelvic region. FIG. 3 shows the cushion 50 from above, showing a generally rectangular region 56 which is the cylindrical knee cushion 56 from above.

Figure 4:
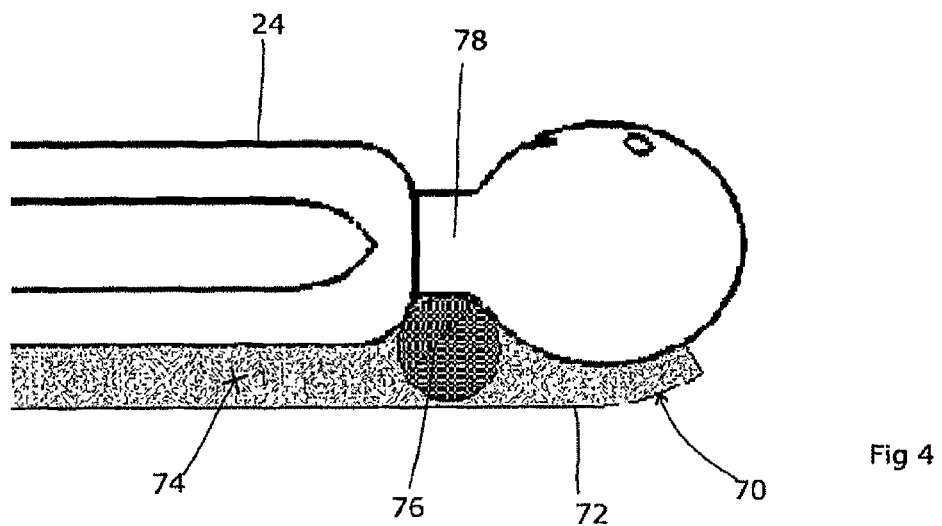
FIG. 4 shows a vertical section through a third embodiment of the invention.

FIG. 4 shows a third embodiment, in which the cushion 70 again includes a hull material 72 and a filling 74, in addition to a neck roll 76 that is located within the cushion 70 so as to support the underneath of the neck 78 of a patient 24. This provides an additional stabilisation of the neck, which is not generally achievable with standard vacuum cushions given that there is little or no access beneath the patient's neck in order to mould the cushion when the patient is lying on it. This can serve to increase a patient's comfort during treatment significantly, which will itself reduce movement of the patient, and could also elevate the neck and shoulders so as to provide better access for the beam during treatment.

Figure 5:
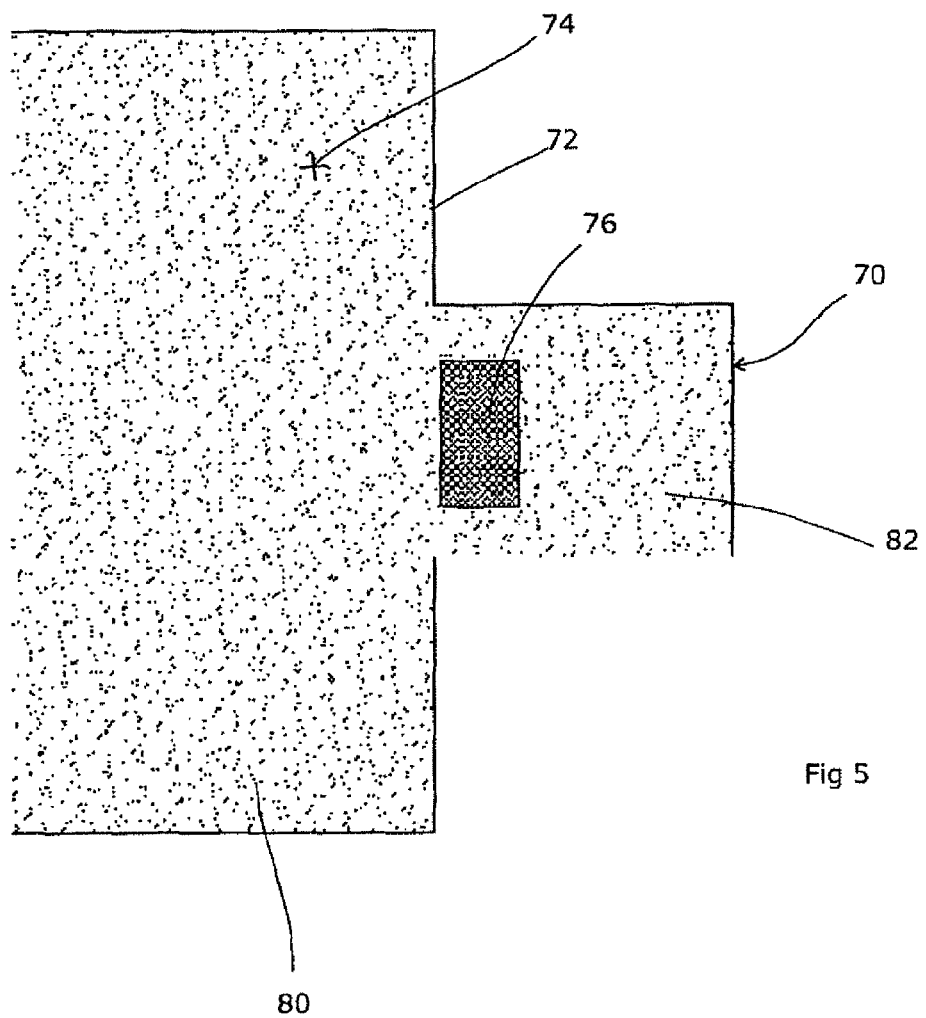
FIG. 5 shows a horizontal section through a third embodiment of the invention.

FIG. 5 shows the cushion 70 from above, and again a rectangular region 76 can be seen indicating the generally cylindrical nature of the neck roll 76. As can also be seen in FIG. 5, the cushion 70 includes a generally wider section 80 designed to accommodate the patient's torso, from which extends a tab section 82 of a generally narrower width to support the patient's head. The neck roll 76 is positioned generally in the junction between the wider section 80 and the curved section 82 as it corresponds to the location of the patient's neck 78. However, it will be appreciated that when the cushion 70 is not evacuated, the neck roll 76 will be moveable within the interior of the hull material 72 and therefore this position will not be fixed.

The features of the above embodiments are not exclusive and could of course be combined, for example to provide a cushion with a neck roll and a shoulder retractor. Equally, other forms of support could be provided, including from specific supports such as lumbar supports and general supports that can be moved around inside the hull in order to position the patient as desired.

Various materials can be used for the cushion, but we prefer a nylon hull coated with a sealable polyurethane-based coating to provide the necessary impermeability to gases that enables a vacuum to be maintained over long periods of time. For the filling material, we prefer polystyrene spheres of a size typically between 0.5 and 3 mm. However, other materials can be adopted as desired.

It will of course be understood that many variations may be made to the above-described embodiment without departing from the scope of the present invention.

Although the present invention has been described with reference to preferred embodiments, workers skilled in the art will recognize that changes may be made in form and detail without departing from the spirit and scope of the invention.

The invention claimed is:

1. A positioning system for a body, comprising;
   a flexible bag of a gas-impermeable material, including a valve to permit evacuation of the interior thereof;
   the bag containing a flowable granular material and at least one bolster free to move within the bag when the bag is not evacuated, so as to support a part of the body.

2. The positioning system according to claim 1 in which the body is at least part of a human form.

3. The positioning system according to claim 1 in which the body is at least part of a patient.

4. The positioning system according to claim 1 in which a size dimension of the bolster is at least 5 times the size dimension of the granular material.

5. The positioning system according to claim 1 in which the bolster includes a generally flat section and an upstanding section extending therefrom.

6. The positioning system according to claim 1 in which the bolster is generally cylindrical in shape.

7. The positioning system according to claim 1 in which the bolster comprises a flexible covering enclosing a granular material.

8. The positioning system according to claim 7 in which the flexible covering is a textile material.

9. The positioning system according to claim 1 in which the bolster is a moulded plastic structure.

10. The positioning system according claim 1 in which the granular material consists of polystyrene spheres.

11. The positioning system according to claim 1 in which the bag is of a nylon material.

12. The positioning system according to claim 11 in which the nylon material is coated with a polyurethane-based coating.

13. The positioning system according to claim 4 in which the bolster includes a generally flat section and an upstanding section extending therefrom.

14. The positioning system according to claim 4 in which the bolster is generally cylindrical in shape.

15. The positioning system according to claim 14 in which the bolster comprises a flexible covering enclosing a granular material.

16. The positioning system according to claim 15 in which the flexible covering is a textile material.

17. The positioning system according to claim 14 in which the bolster is a moulded plastic structure.

18. The positioning system according claim 1 in which the granular material consists of polystyrene spheres.

\* \* \* \* \*